(12) United States Patent
Gonzalez

(10) Patent No.: US 10,220,190 B2
(45) Date of Patent: Mar. 5, 2019

(54) DELIVERY CATHETER WITH FIXED GUIDEWIRE AND BEVELED ELLIPTICAL PORT

(71) Applicant: Luis Fernando Gonzalez, Gladwyne, PA (US)

(72) Inventor: Luis Fernando Gonzalez, Gladwyne, PA (US)

(73) Assignee: Culvert Therapeutics, LLC, Youngsville, NC (US)

( * ) Notice: Subject to any disclaimer, the term of this patent is extended or adjusted under 35 U.S.C. 154(b) by 0 days.

(21) Appl. No.: 15/392,116

(22) Filed: Dec. 28, 2016

(65) Prior Publication Data
US 2017/0182296 A1    Jun. 29, 2017

Related U.S. Application Data

(60) Provisional application No. 62/271,875, filed on Dec. 28, 2015.

(51) Int. Cl.
*A61M 25/09* (2006.01)
*A61M 25/00* (2006.01)
(Continued)

(52) U.S. Cl.
CPC ........ *A61M 25/09* (2013.01); *A61M 25/0068* (2013.01); *A61M 25/0082* (2013.01); *A61M 25/0097* (2013.01); *A61M 31/005* (2013.01); *A61M 2025/0186* (2013.01); *A61M 2025/1056* (2013.01); *A61M 2210/127* (2013.01)

(58) Field of Classification Search
CPC .. A61M 2025/0186; A61M 2025/1056; A61M 2210/127; A61M 25/0068; A61M 25/0082; A61M 25/0097; A61M 25/09; A61M 31/005
See application file for complete search history.

(56) References Cited

U.S. PATENT DOCUMENTS

| | | |
|---|---|---|
| 4,986,814 A | 1/1991 | Burney et al. |
| 5,114,414 A | 5/1992 | Buchbinder |

(Continued)

FOREIGN PATENT DOCUMENTS

WO    WO-2017117190 A1    7/2017

OTHER PUBLICATIONS

International Search Report and Written Opinion dated Mar. 16, 2017 for International PCT Patent Application No. PCT/US2016/068825.

(Continued)

*Primary Examiner* — Imani Hayman
(74) *Attorney, Agent, or Firm* — Myers Bigel, P.A.

(57) ABSTRACT

A catheter includes a catheter body having a proximal end, a beveled distal end, and a lumen therethrough. The beveled distal end defines an elliptical port for releasing contrast or other media through the lumen and from the elliptical port. The catheter may also be used delivering devices or for aspirating or extracting materials from the vasculature or other body lumens. A fixed guidewire extends distally from the distal end of the catheter body, typically from the distal-most edge of the elliptical port. The fixed wire is typically malleable so that it can be manually formed into a desired shape. The elliptical port may be flat or concave.

10 Claims, 6 Drawing Sheets

(51) Int. Cl.
*A61M 25/01* (2006.01)
*A61M 31/00* (2006.01)
*A61M 25/10* (2013.01)

(56) References Cited

U.S. PATENT DOCUMENTS

| | | |
|---|---|---|
| 5,180,364 A | 1/1993 | Ginsburg |
| 6,206,852 B1 * | 3/2001 | Lee ................... A61M 25/0069 604/96.01 |
| 6,936,065 B2 | 8/2005 | Khan et al. |
| 7,224,250 B2 | 5/2007 | Nemoto et al. |
| 8,764,724 B2 | 7/2014 | Itou et al. |
| 8,850,960 B2 | 10/2014 | Biesheuvel et al. |
| 2002/0099433 A1 | 7/2002 | Fischell et al. |
| 2003/0144628 A1 | 7/2003 | Sirimanne |
| 2007/0088273 A1 | 4/2007 | Rafi |

OTHER PUBLICATIONS

Sarno, et al. The coronary Stent-on-a-Wire (SOAW). EuroIntervention. Aug. 2010;6(3):413-7. doi: 10.4244/EIJV6I3A68.

* cited by examiner

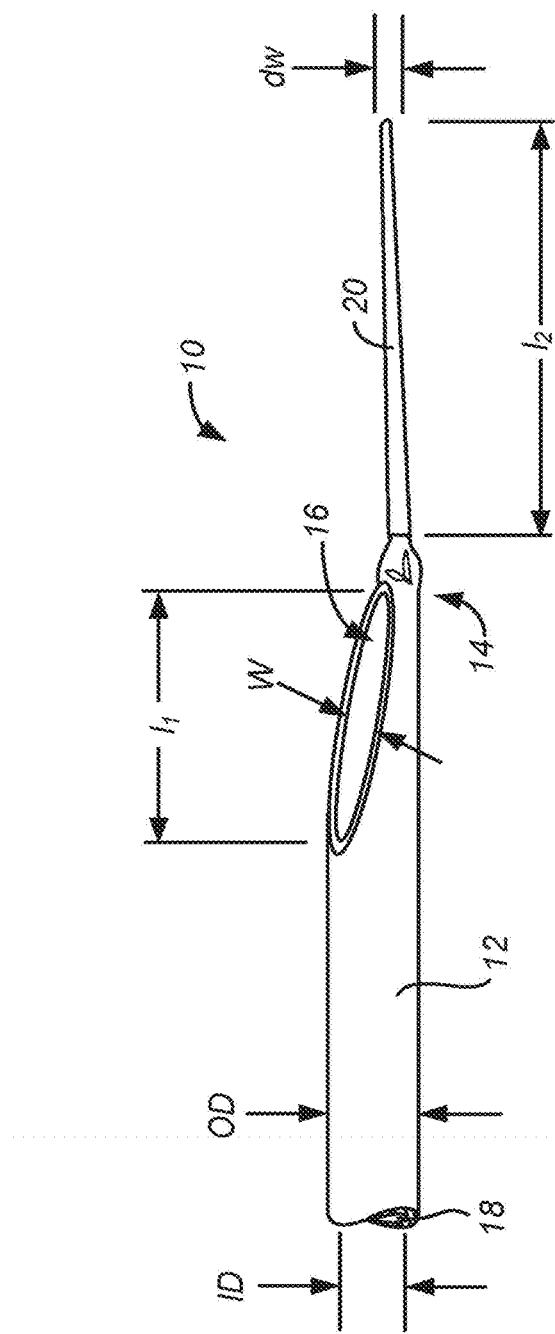
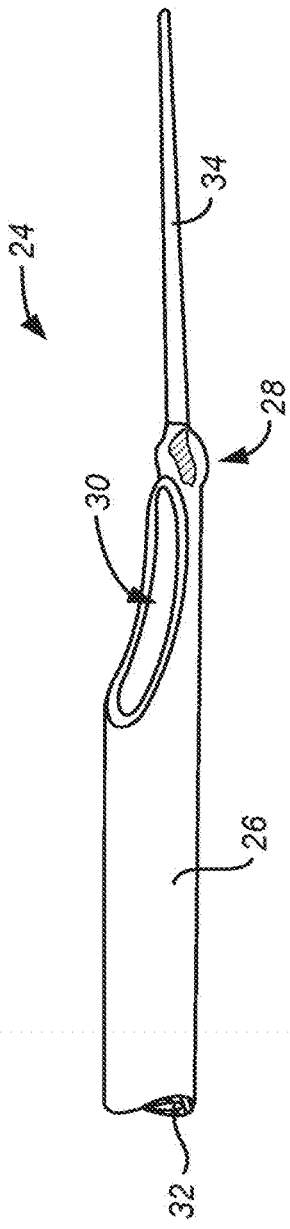
FIG. 2
FIG. 3

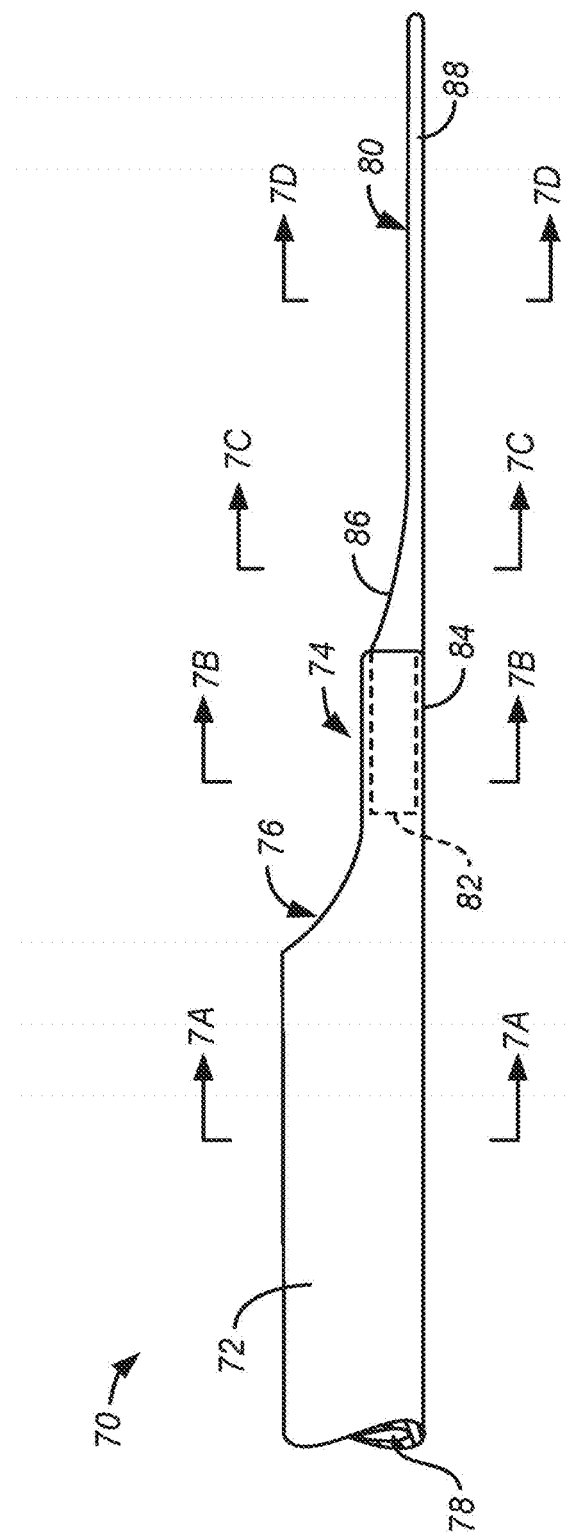
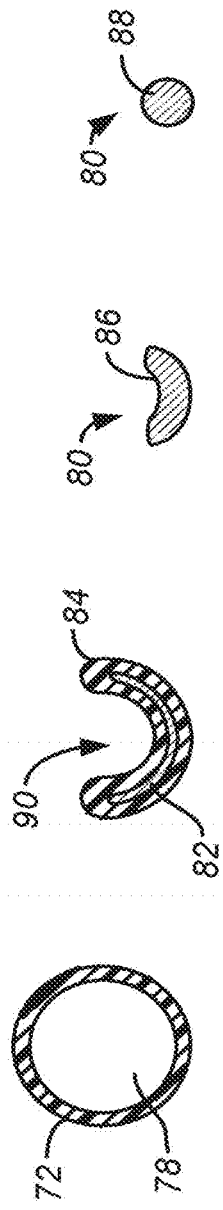

DELIVERY CATHETER WITH FIXED GUIDEWIRE AND BEVELED ELLIPTICAL PORT

CROSS-REFERENCE TO RELATED APPLICATIONS

This application claims the benefit of Provisional Application No. 62/271,875, filed Dec. 28, 2015, the entire content of which is incorporated herein by reference.

BACKGROUND OF THE INVENTION

1. Field of the Invention

The present invention relates generally to medical devices and methods. More particularly, the present invention is directed at guide wires and their incorporation into diagnostic and therapeutic (multipurpose) catheters.

Currently, diagnostic catheters are steered by a first wire (typically referred to as a moveable guidewire) that is disposed in a lumen running the entire catheter length, typically 90-100 cm. The first wire is longer than the catheter and extends distally from the catheter tip by a variable length, usually from 5-7 cm. The diagnostic catheters are navigated "over the wire" (OTW) to a target vessel, typically a coronary or cerebral artery in an angiography procedure. The purpose of the wire is to steer the catheter as it is advanced through the artery. The wire is advanced first, and the catheter is then advanced over the slides over wire which provides a track for guiding the catheter. This procedure is repeated until the catheter reaches the desired or "target" location, and the wire is then pulled back in the case of an angiography catheter to open the lumen for introducing contrast media.

After the initial angiography or other diagnostic procedure is complete, a balloon or other therapeutic catheter may be "exchanged" for the diagnostic catheter by replacing the first wire with a longer, typically 260-300 cm, exchange wire. The diagnostic catheter is withdrawn over the exchange wire, and the therapeutic catheter then advanced over the exchange wire. The exchange wire must be sufficiently long to allow the physician to be able to grasp some portion of the wire as the diagnostic catheter is withdrawn as well as when the therapeutic catheter is advanced.

Having the entire length of the first wire present in the diagnostic catheter can be disadvantageous in several ways. For example, the wire reduces the flexibility of the catheter making the diagnostic catheter difficult to navigate through tortuous anatomy. Additionally, the space between the inner diameter (ID) of the diagnostic catheter lumen and the outer diameter (OD) of the first wire creates a "shelf". This shelf can "catch" on the ostium of branch vessels as they take off from the main vessel along the catheter's course.

Currently guidewires used in diagnostic procedures have an outside diameter (OD) from 0.035 inch to 0.038 inch, reducing the flexibility of the diagnostic catheter as it is advanced through the vasculature. One reason for using such larger, stiffer wires is to decrease risk of the "shelving effect" between the catheter and the wire. Using a larger diameter wire reduces the spacing between the catheter lumen's ID and the wire's OD which in turn reduces the height of the shelf and the risk that catheter will engage branch vessels as the catheter is advanced. Such larger diameter wires, however, have the disadvantage that they are less flexible, making navigation of the wires and catheters even more difficult.

A further difficulty with conventional angiography and other diagnostic catheters arises when the first wire is pulled back during advancement of the catheter, Such pull back generates a negative pressure (similar to pull back of a plunger in a syringe) which can release air bubbles from the catheter lumen. The air bubbles can travel distally into the blood stream creating air emboli and potentially causing cause strokes.

Two techniques are commonly used to mitigate air bubbles from migrating distally when the wire is removed: The first technique is known as "double flush" technique in which aspiration with a syringe is performed twice, before establishing anterograde flow; after the second aspiration, the catheter is flushed with heparinized saline and contrast dye. The second technique uses continuous heparinized saline infusion, and when the wire is removed, the rotatory hemostatic valve (RHV) is left open allowing back bleeding; this retrograde bleeding will remove the air bubbles, then the RHV is flushed with saline, and finally anterograde flow is established. Both these techniques add complexity and risk to the procedures.

Most wires have an atraumatic "J" tip, in order to deflect the wire away from vessel walls, and to prevent the wire from dissecting the vessel wall when resistance is found. A less common wire has a straight tip but is malleable, giving the operator the ability to reform the tip, into a desired shape, based on the architecture of the vessel that attempted to be catheterized and to facilitate the a-traumatic catheterization of the vessel. Once the wire "makes a curve", the catheter is advanced OTW to the desired location.

With current technology the proximal end of the wire is manually rotated by hand with a "pill-roll" finger movement or using a torque device, a collet, that facilitates the necessary grasp to make a clock and counter-clock rotation of the wire. With current diagnostic catheter technology, it is also necessary to pull the wire out prior to the contrast injection which is necessary in order to opacify the target. Both these steps complicate current angiography protocols.

A majority of diagnostic catheters have angled tips, called multipurpose (MP) catheters. A 45° degree MP tip is bent at a 45° degree angle relative to the central axis of the catheter body. The purpose of an angled tip is to allow engaging the origin of larger vessels and then to advances the wire from within. Once the target has been reached, the catheter can slide over the wire. Ideally, MP catheter tips are left along the axis of the target vessel. On the other hand, if a MP catheter is in a straight segment, the angled tip will be against the wall, as shown in FIG. 1, with the potential to cause a dissection to the vessel wall, especially if the wire is advanced forward.

For these reasons, it would be desirable to provide improved guide wire structures and methods for their use in introducing angiography and other vascular diagnostic and therapeutic catheters. It would be particularly desirable to provide diagnostic catheter structures and methods for their use which can eliminate the need to periodically pull back the guide wire as the catheter is advanced, thus simplifying the procedure and lessening the risk of introducing air embolism. It would further be desirable to eliminate any need for more than one lumen in the diagnostic catheter. At least some of these objectives will be met by the inventions described hereinafter.

2. Description of the Background Art

The disclosures described below are relevant background to the present invention:

U.S. Pat. No. 5,114,414 describes a system that includes a multi-lumen catheter. One of those lumens is closed at the distal end, with an "antenna" that comes out the distal closed end. The stated purpose of the wire is to protect the arterial lumen. The other lumens are multipurpose. i.e. to host a wire, instruments, or the like. Having multiple lumens can lead to an undesirable overall increase in the diameter of the catheter.

U.S. Pat. No. 8,764,724 describes a diagnostic or aspiration catheter (FIGS. 7A, 7B and 8) with an obliquely inclined tip having a wire lumen 92 fixed thereto and a guide wire extending therethrough. The patent proposes a multi lumen catheter for coronary application. My invention describes a single lumen catheter. One of the elements of this co-axial system described here includes a beveled catheter on both ends distal and proximal. The proximal segment of the double beveled catheter is attached to a wire that is embedded for the entire length. The wire does not arise from the beveled tip, my invention describes a wire embedded only on the distal tip of a beveled catheter, the one that is presented here comes from a separate element from one of the lumens within the coaxial system. Shows a suction catheter (FIGS. 7A, 8) with an obliquely inclined tip having a wire lumen 92 fixed thereto and a guide wire extending therethrough. The beveled tip increases the cross sectional diameter of the catheter.

U.S. Pat. No. 7,224,250 describes a two lumen aspiration catheter with one lumen having a beveled tip and a second, shorter lumen, providing a rapid exchange system where the wire is not part of the system. There is a shorter catheter that is glued to the distal end of the aspiration catheter; this second lumen allows the passage of a wire. These catheters are advanced to a target location after an initial catheter reaches the target. The initial catheter is then withdrawn and replaced with a second catheter.

U.S. Pat. No. 8,850,960 describes a beveled catheter for arterial puncture like a needle, followed by the insertion of a dilator. The catheter uses a wire that travels within the entire lumen of the catheter but which is not embedded. The purpose is mainly for access and not for navigation aspiration or radiographic contrast injection.

A stent on a wire is described in Sarno et. al. (2010) EuroIntervention 6:413-417. The wire is attached the entire length of the stent, and the device is not intended for primary navigation and requires a separate guiding catheter. The "stent on a wire" does not have a beveled tip.

FIG. 1 shows a prior art MP catheter in a straight section of an artery with a distal tip of the catheter urged against the arterial wall. A magnification in the lower left corner shows deformation of the wall by the catheter tip.

SUMMARY OF THE INVENTION

The present provides improved angiography and other diagnostic and therapeutic catheters and methods for their use. In particular, a diagnostic catheter includes a catheter body having a proximal end, a beveled distal end, and a lumen therethrough. The beveled distal end defines an elliptical port for releasing a radiopaque medium infused through the lumen, and a fixed guidewire extends distally from the distal end of the catheter body. The beveled distal tip improves aspiration capabilities when compared to a conventional cylindrical catheter. The distal end of the catheter body typically terminates in a fixed distal wire or other guiding tip adjacent to a distal-most edge of the elliptical port, and the fixed wire usually extends distally from the distal tip. The fixed wire may be embedded in the distal end of the catheter boy and may be malleable so that it can be manually formed into a desired shape. The elliptical port may have a flat boundary or alternatively have a concave boundary. Usually, the catheter body comprises or consists of a tubular member having a single lumen therethrough with a proximal end of the wire embedded into and/or overlapping with a distal portion of the tubular member, typically by a distance sufficient to allow secure fixation of the wire to the member, typically being in the range from 0 to 25 mm, usually being from 1 mm to 10 mm. Typically, the wire will not extend proximally beyond this limited fixation location, and often the remainder of the length of the tubular member will be free from all reinforcement, i.e. being an unreinforced polymeric tube. Further optionally, a valve or hub may be positioned at the proximal end of the catheter body, typically including a three-way valve or stopcock to allow rapid switching between contrast injection and the injection of heparinized saline, as needed.

Advantages of the designs of the present invention include: (1) Having the catheter and the wire integrated, results in easier introduction through the access sheath; the wire will lead the path for the catheter to pierce the sheath valve; (2) Having a larger cross sectional diameter permits the use of a secondary buddy wire within the entire catheter lumen if needed for difficult access; (3) having a beveled tip increases, the aspiration power of the catheter, facilitating the extraction of foreign elements such as clots or other material; (4) This design will allow the use of smaller embedded diameter wires with no need for the catheter to be double flushed or wait for back bleeding after the wire is removed; (5) The design expedites the procedure by using a three-way stopcock to rapidly switch between contrast injection and the injection of heparinized saline as needed without requiring periodic retraction of the wire to open the catheter lumen to allow contrast injection; (6) Facilitating guidance of the catheter by applying torque on the catheter itself which is transmitted to the distal wire embedded in the catheter tip (in contrast to indirect torquing of a separate wire in a lumen of the angiography catheter): (7) A beveled catheter tip will be better anatomically suited on straight vessel segments than the current multipurpose catheters; (8) A beveled catheter tip will facilitate advancement preventing the distal end of the catheter from "catching" at the ostium of branching arteries as the catheter is advanced; (9) A beveled tip provides a larger cross diameter (larger extraction area) enhancing aspiration in comparison to the current technology; (10) A more concave beveled tip will further increase the area and aspiration efficiency; (11) The design reduces the "shelf" which is created by a difference in diameter between the wire's OD and the catheter's ID; and (12) The beveled tip compensates for the decrease in the catheter diameter caused by having the wire embedded in the catheter, while still providing a larger cross sectional diameter.

In a first specific aspect, a diagnostic or therapeutic catheter according to the present invention comprises a catheter body having a proximal end, a beveled distal end, and a lumen therethrough. The beveled distal end defines an elliptical port configured to release a radiopaque medium infused through the lumen, and a fixed guidewire extending distally from the distal end of the catheter body.

In particular embodiments, the distal end of the catheter body terminates in a distal tip adjacent to distal-most edge of the elliptical port and wherein the fixed wire extends distally from the distal tip. The fixed wire may be malleable so that it can be manually formed into a desired shape. The elliptical port may be concave or scalloped, or the elliptical port may be flat. The elliptical port may be further configured to delivering other devices or serve as a conduit for extracting material through the lumen.

In certain preferred embodiments, the fixed guidewire may be embedded in the distal end of the catheter body. For example, the fixed guidewire may be embedded in a length of the distal end of the catheter body of 25 mm or less with the remainder of the length of the catheter body be free of the fixed guidewire. In more specific embodiments, the fixed guidewire may embedded in a length of the distal end of the catheter body in the range from 1 mm to 10 mm. In a particularly preferred embodiment, the beveled distal end of the catheter body and an embedded proximal portion of the fixed wire together form a trough which extends from the elliptical port.

In a second specific aspect, a method for performing angiography comprises providing an angiography catheter having a proximal end, a beveled distal end, a lumen therethrough, and a fixed guidewire extending distally from the distal end, wherein the beveled distal end defines an elliptical port. The catheter is advanced through an aorta, and the catheter body is torqued while advancing to steer the guidewire into a branch vessel. After the elliptical port is positioned in a target vessel, contrast media may through the lumen into the branch vessel. Optionally, the angiography catheter may be introduced through an access sheath into the aorta without an introducer.

BRIEF DESCRIPTION OF THE DRAWINGS

FIG. 2 illustrates a first embodiment of a distal end of an angiography catheter having a straight or flat elliptical contrast release and/or aspiration port constructed in accordance with the principles of the present invention.

FIG. 3 illustrates a second embodiment of a distal end of an angiography catheter having a concave or "scalloped" elliptical contrast release and/or aspiration port constructed in accordance with the principles of the present invention.

FIG. 7 illustrates a third embodiment of a distal end of an angiography catheter constructed in accordance with the principles of the present invention having a quill-shaped proximal end embedded in the distal tip of the catheter body.

FIGS. 7A-7D are cross-sectional views taken along lines 7A-7A, 7B-7B, 7C-7C, and 7D-7D, respectively, of FIG. 7.

DETAILED DESCRIPTION OF THE INVENTION

Figure 1:
FIG. 1 shows a prior art MP catheter in a straight section of an artery with a distal tip of the catheter urged against the arterial wall. A magnification in the lower left corner shows deformation of the wall by the catheter tip.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

FIG. 2 illustrates a first exemplary catheter 10 having a catheter body 12 with a beveled distal tip 14 with fixed guidewire 20 extending distally from an elliptical port 16 at the distal end of a central lumen 18. While particularly intended for use as an angiography catheter, the catheters of the present invention may also find use in other diagnostic procedures, particularly those relying on intravascular deliver of contrast media or other substances, as well as in therapeutic interventions, such as aspiration of blood clots and/or foreign bodies or as a conduit for infusion of drug and/or and other substance delivery.

Exemplary dimensions for the catheter 10 when used for angiography are set forth in Table 1 below.

TABLE 1

Exemplary Dimensions for Angiography Catheter

| Dimension | Broad Range | Exemplary Range |
|---|---|---|
| Catheter Body Length | 50 cm-300 cm | 90 cm-130 cm |
| Catheter OD | 1 mm-10 mm | 1 mm-3 mm |
| Catheter Lumen ID | 0.5 mm-9.5 mm | 0.5 mm-2.5 mm |
| Distal Port Length $\ell_1$ | 1.4 mm-15 mm | 3 mm-6 mm |
| Distal Port Width $w$ | 0.3 mm-1.5 mm | 0.4 mm-1.2 mm |
| Wire Length $\ell_2$ | 3 cm-30 cm | 5 cm-20 cm |
| Wire Diameter $d_W$ | 0.2 mm-1 mm | 0.3 mm-0.6 mm |

The distal end of the catheter 10 differs from those of conventional angiography catheters in at least three particular respects. First, the catheter has a fixed guidewire allowing the catheter to be advanced through the vasculature without using a separate, moveable guidewire as discussed in the Background section above. Elimination of the moveable guidewire is advantageous as it both decreases the stiffness of the catheter as it is advanced and reduces the risk of generating air emboli associated with guidewire retraction. Elimination of the moveable guidewire also reduces the risk of clot formation since availability of the open lumen allows continuous infusion of heparinized saline. Conventional angiography catheters with moveable guidewires allow only intermittent anterograde infusion. Second, location of a bevel immediately proximal to the fixed guidewire attachment location provides a very smooth, tapered profile that facilitates catheter advancement through tortuous regions of the vasculature. In particular, the shelf present at the junction of a moveable guidewire and a catheter tip in a conventional angiography system is eliminated. Third, the beveled distal tip allows formation of an elliptical port which is larger than a circular port formed orthogonally across the tip of the catheter as with most conventional catheters. The larger area of the elliptical port lowers flow resistance to the delivery of contrast media and other substances delivered through the catheter lumen in addition having a larger cross sectional area increases the aspiration power compared to a conventional cylindrical catheter.

By "elliptical," it is meant that the port will have a larger axial dimension (length) than lateral dimension (width). When measured across the open port area, the lateral dimension may be as large as the inner diameter of the catheter body lumen measured at the location of the port, typically being at least 50% of the width, usually being at least 75% of the width, and typically being at least 90% of the width. The axial dimension (length) will be typically be at least 1.5 fold greater that the maximum lateral dimension (width), usually being at least 3 fold grater, often being at least 5 fold greater.

The catheter body 12 may be constructed by polymer extrusion or three-dimensional printing in accordance with well known medical catheter fabrication techniques. The catheter body may optionally be reinforced to enhance torqueability, e.g. with braids, helical wires, coils, or other well-known reinforcement techniques. The fixed wire may also be constructed by known techniques for fabricating fixed and moveable guidewire, typically having a coiled exterior shell and a malleable internal core. The wire will be attached to the distal tip of the catheter body, preferably at the distal-most location on the distal tip, i.e. at the distal end of the elliptical port 16. Usually, a proximal portion of the wire 20 will be fixed to the catheter body by embedding a length in a wall of the body. The embedded length will usually be from 1 to 25 mm, usually being from 3 mm to 10 mm. Embedding may conveniently be achieved by wrapping a distal portion of the catheter wall around the proximal end or shank of the guidewire and then heat or ultrasonically welding the resulting junction. Alternatively or additionally adhesives, staples, rivets, and other external fasteners could be employed.

Referring now to FIG. 3, a second exemplary catheter 24 comprises having a catheter body 26 with a beveled distal tip 28 with fixed guide 34 extending distally from an elliptical port 30 at the distal end of a central lumen 32. The catheter 24 is similar in most or all respects to catheter 10 except for the shape of the elliptical port 30. While elliptical port 16 has a generally flat or straight planar opening (i.e. the periphery of elliptical port 16 lies in a flat plane), elliptical port 30 is non-planar with a concave or scalloped periphery. Such a concave or scalloped periphery increases the open port area available for release and/or aspiration of contrast media or other substances and can thus decrease flow resistance and/or increase flow rate through the port.

Other advantages of the more concave bevel include (1) a concave bevel will reduce trauma as the catheter passes by the takeoff of other vessels, (2) a concave bevel, rather than a straight bevel profile, will increase the cross sectional diameter of the catheter even further, increasing the aspiration power even further, (3) the proximal end of the catheter has a "torpedo" like design proximal to the female luer connector (FIG. 4), with low profile wings encircling the catheter, and (4) the design will facilitate torquing of the entire catheter-wire device.

Figure 4:
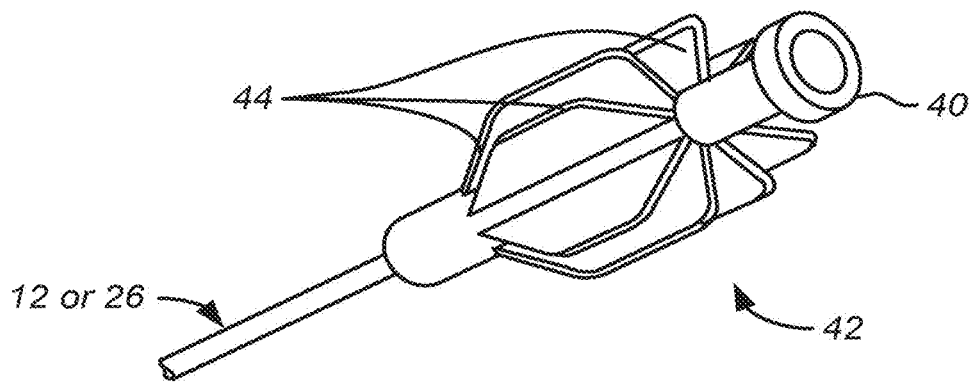
FIG. 4 illustrates an exemplary proximal end or hub of an angiography catheter having a finned or "torpedo" luer fitting constructed in accordance with the principles of the present invention.

FIG. 4 illustrates an exemplary proximal hub 42 on the proximal end on the catheter body 12 or 26. The proximal hub will typically have a luer or other conventional fitting 40 at its proximal terminus for connection to a source of contrast media or other substance to be delivered as described further below. Conveniently, the hub may have fins 44 (referred to as a "torpedo" structure) or other gripping features to facilitate manipulation and torquing by the physician to steer the catheter 10 or 24 as it is advanced through the vasculature.

Figure 5:
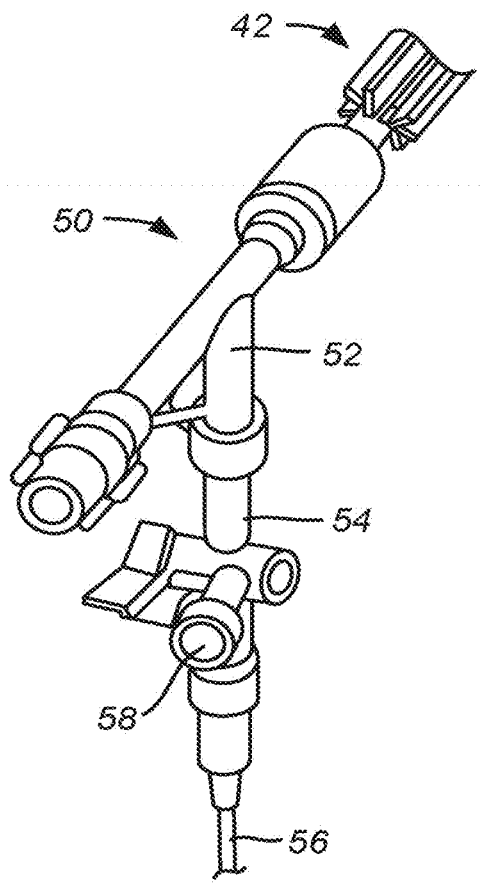
FIG. 5 illustrates connection of the luer fitting of FIG. 4 to a source of saline with a septum for injecting contrast medium into the angiography catheter.

FIG. 5 illustrates connection of the hub 42 of catheter 10 or 24 to a fitting 50 used to introduce heparinized saline and contrast media. The fitting 50 has a side branch 52 connected to a three-way valve 54. Heparinized saline can be fed into the catheter by a saline line 56 connected to one port of the three-way valve. Contrast media can be injected through a septum 58 connected to the other port of the three-way valve using a syringe.

Figure 6:
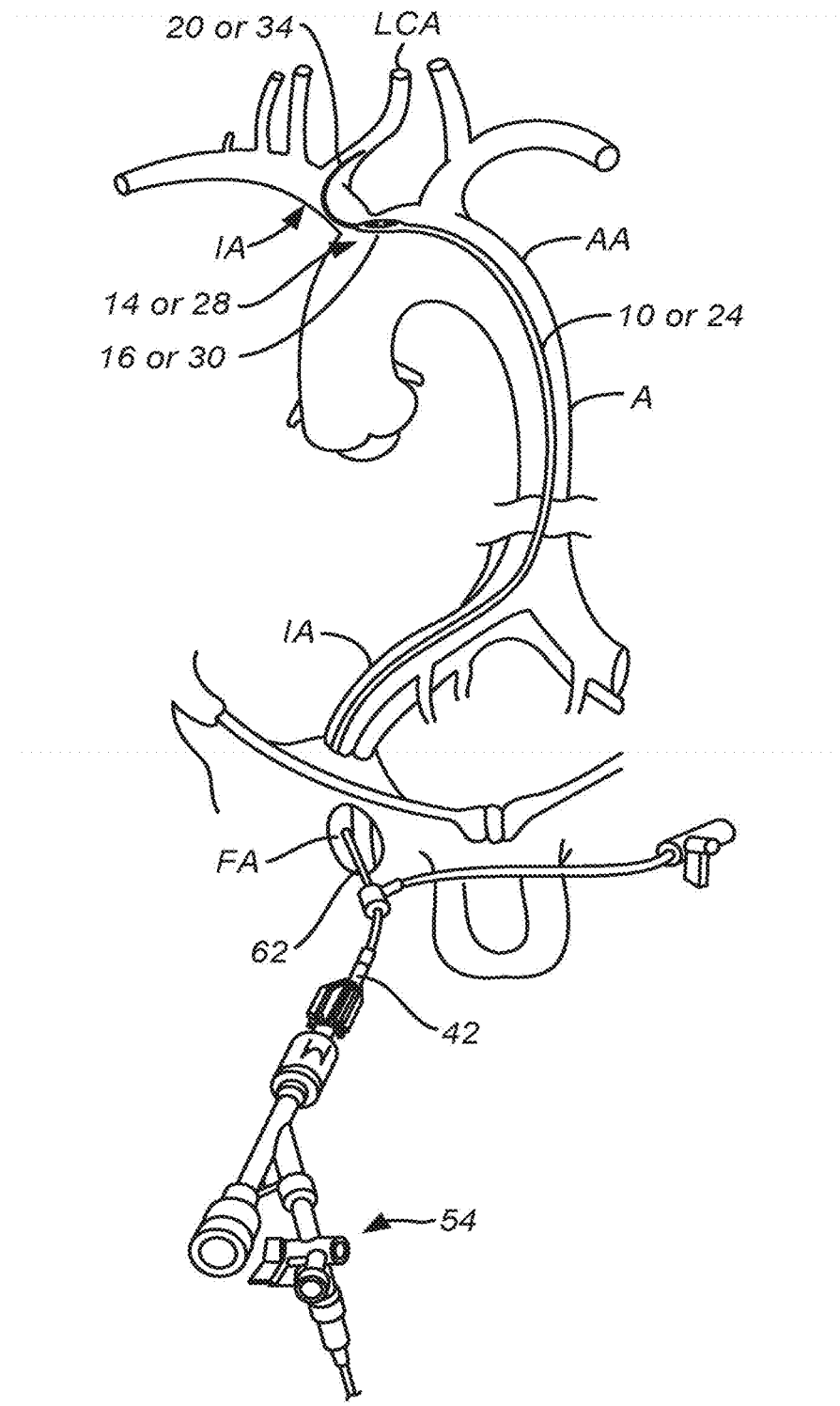
FIG. 6 illustrates introduction of an angiography catheter of the present invention to a left common carotid artery via an innominate artery in a "bovine" aortic arch type.

Referring now to FIG. 6, the beveled tips 14 and 28 of catheters 10 and 24 of the present invention will facilitate atraumatic advancement of the catheter through the ostium of other vessels. The olive, beveled catheter tip facilitates placement of the catheter on straight segments. This differs from current technologies where an angled catheter tip faces against the arterial wall directly as shown in FIG. 1. The catheters of the present invention with an embedded wire at the beveled tip can eliminate the need to remove the wire every time the catheter is advanced, thus preventing the introduction of air bubbles and other risks of repeated catheter removals and insertions. The malleable distal wire that can be reformed into any desired shape or angle, according to the particular architecture of the vessel to be catheterized. Not having to remove the wire every single time prior to contrast injection expedites the procedure.

The diagnostic catheters of the present invention allow the injection of contrast material to opacify intravascular structures and to then allow continuous heparinized saline infusion to prevent clot formation, or to aspirating either by hand with a syringe or an aspiration pump, by a simple rotation of the three-way valve 54 since there is no need to remove the wire (this is not possible with conventional angiography catheters where the presence of a movable wire in the central lumen inhibits contrast injection). Combining the catheter body and the wire in one device improves the torquing ability of the assembly as a whole. In conventional angiography catheters, only the wire is torqued by hand or by using a collet that grasps the wire. Using either approach, rotating an MP catheter is difficult due to the tip angle. In cases of extreme tortuosity is possible to advance a second wire through the main lumen of the catheter as a "buddy wire" while the embedded wire stabilizes the apparatus.

Figure 6A:
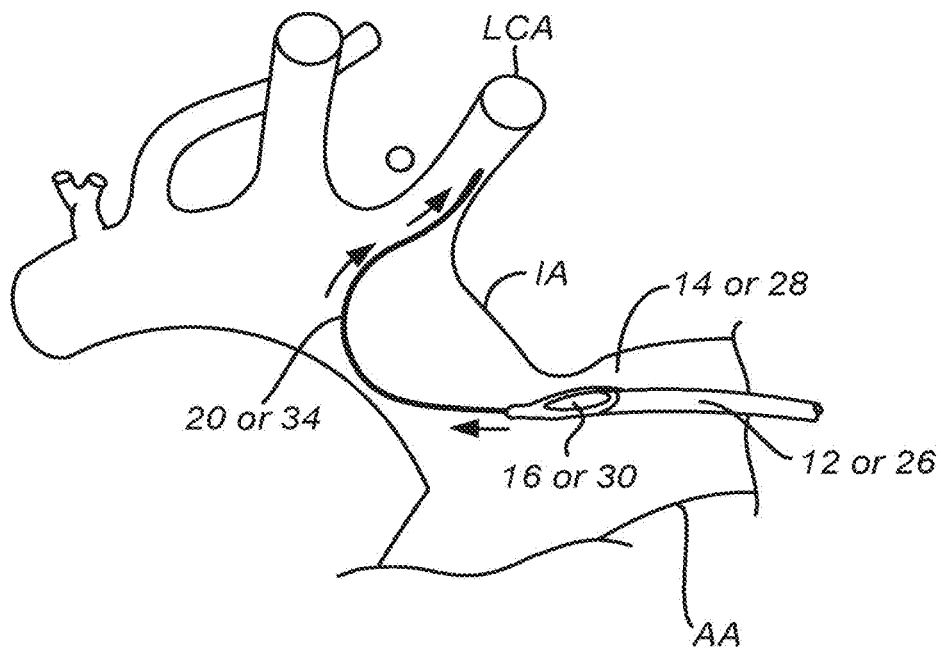
FIG. 6A illustrates introduction of an angiography catheter of the present invention to a left common carotid artery similarly to FIG. 6 where the guidewire tip has a more aggressive bend.

As shown in FIGS. 6, and 6A, an access sheath 62 is placed in the femoral artery in a patient's groin. The catheter 10 or 24 is advanced through the iliac artery IA and upward through the descending aorta A until reaching the aortic arch AA. The fixed wire 20 or 34 can be pre-shaped to allow the distal tip 14 or 28 to be torqued to steer the wire into the innominate artery and then into the target left common carotid artery LCA. FIGS. 6 and 6A show a bovine variant of the aortic anatomy which presents particular placement challenges. Once the port 16 or 30 is advanced past the os of the target left common carotid artery LCA, the contrast media can be delivered and angiography performed.

Figure 6B:
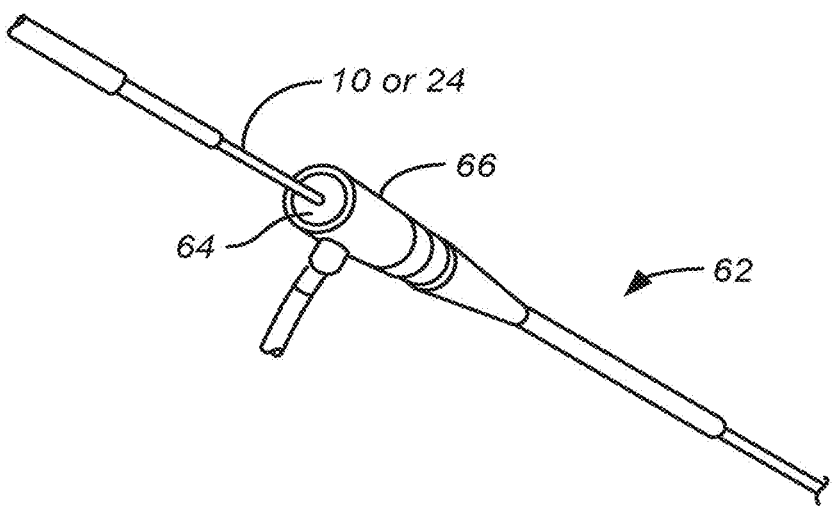
FIG. 6B illustrates introduction of an angiography catheter of the present invention through the access sheath by piercing the valve without the need for an introducer.

FIG. 6B illustrates placement of the catheter 10 or 24 through a septum 64 of a hub 66 of the access sheath 62. The beveled tip with fixed guide wire of the present invention facilitates the introduction of the distal tip of the catheter through the access sheath without the need for an introducer.

Referring now to FIGS. 7 and 7A-7D, a third exemplary catheter 70 comprises a catheter body 72 with a beveled distal tip 74 with fixed guide wire 80 extending distally from an elliptical port 76 at the distal end of a central lumen 78. The proximal portion (not shown) of catheter 70 may be similar or identical in at least most respects to the proximal portions catheters 10 and 24. The distal portion of catheter 70 will, in contrast, differ in significant respects. The fixed wire 80 will has a shank region 82 with an arcuate or semi-circular cross-section, as best seen in FIG. 7B, The semi-circular shank is embedded in a C-shaped distal region of the catheter body 72, as also best seen in FIG. 7B. The combined cross-sections of the shank 82 and the C-shaped region 84 form a trough which open the distal end of the elliptical port 76 to further reduce flow resistance when compared to that of the ports of catheters 10 and 24 described previously. The fixed wire 80 extends distally from the embedded shank region 82 and undergoes a gradual transition through a transition region 68 (FIG. 7C) until it reaches a generally circular profile 88 (FIG. 7D) over its distal portion.

While preferred embodiments of the present invention have been shown and described herein; it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A diagnostic or therapeutic catheter comprising:
   a catheter body having a proximal end, a beveled distal end, and a lumen therethrough, wherein the beveled distal end defines an elliptical port configured to release a radiopaque medium infused through the lumen; and
   a fixed guidewire extending distally from the beveled distal end of the catheter body, wherein the fixed guidewire is embedded in the beveled distal end of the catheter body, and the beveled distal end of the catheter body and an embedded proximal portion of the fixed wire together form a trough which extends from the elliptical port.

2. The diagnostic or therapeutic catheter as in claim 1, wherein the beveled distal end of the catheter body terminates in a distal tip adjacent to a distal-most edge of the elliptical port and wherein the fixed guidewire extends distally from the distal tip.

3. The diagnostic or therapeutic catheter as in claim 1, wherein the fixed guidewire is malleable so that it can be manually formed into a desired shape.

4. The diagnostic or therapeutic catheter as in claim 1, wherein the elliptical port is concave.

5. The diagnostic or therapeutic catheter as in claim 1, wherein the elliptical port is flat.

6. The diagnostic or therapeutic catheter as in claim 1, wherein the elliptical port is further configured to deliver other devices or serve as a conduit for extracting material through the lumen.

7. The diagnostic or therapeutic catheter as in claim 1, wherein the fixed guidewire is embedded in a length of the beveled distal end of the catheter body of 25 mm or less with the remainder of the length of the catheter body being free of the fixed guidewire.

8. The diagnostic or therapeutic catheter as in claim 7, wherein the fixed guidewire is embedded in a length of the beveled distal end of the catheter body in the range from 1 mm to 10 mm.

9. A method for performing angiography, said method comprising;
   providing an angiography catheter having a catheter body with a proximal end, a beveled distal end, a lumen therethrough, and a fixed guidewire extending distally from the beveled distal end, wherein the beveled distal end defines an elliptical port, and wherein the fixed guidewire is embedded in the beveled distal end of the catheter body, and the beveled distal end of the catheter body and an embedded proximal portion of the fixed guidewire together form a trough which extends from the elliptical port;
   advancing the catheter through an aorta;
   torquing the catheter body while advancing to steer the guidewire into a branch vessel;
   delivering contrast media through the lumen into the branch vessel.

10. The method for performing angiography as in claim 9, further comprising introducing the angiography catheter through an access sheath into the aorta without an introducer.

* * * * *